United States Patent
Nagata et al.

(10) Patent No.: US 9,480,814 B2
(45) Date of Patent: Nov. 1, 2016

(54) METHOD OF PRODUCING CATHETER TUBE AND CONTINUOUS BODY OF THE SAME

(71) Applicant: TERUMO KABUSHIKI KAISHA, Shibuya-ku (JP)

(72) Inventors: Hideto Nagata, Shizuoka (JP); Katsunori Ebata, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 284 days.

(21) Appl. No.: 14/084,111

(22) Filed: Nov. 19, 2013

(65) Prior Publication Data
US 2014/0142551 A1 May 22, 2014

(30) Foreign Application Priority Data
Nov. 20, 2012 (JP) .................. 2012-254638

(51) Int. Cl.
A61M 25/16 (2006.01)
A61M 25/00 (2006.01)

(52) U.S. Cl.
CPC ..... *A61M 25/0014* (2013.01); *A61M 25/0009* (2013.01); *A61M 25/0012* (2013.01); *A61M 25/0053* (2013.01); *A61M 25/0054* (2013.01); *Y10T 29/49826* (2015.01)

(58) Field of Classification Search
CPC ......... A61M 25/001; A61M 25/0015; A61M 25/0009; A61M 25/0014
USPC .............. 156/304.2, 304.3; 264/152, 632; 604/93.01, 264, 523, 524
See application file for complete search history.

(56) References Cited

U.S. PATENT DOCUMENTS

| | | | | |
|---|---|---|---|---|
| 6,280,545 B1 * | 8/2001 | Kanesaka | ......... | A61M 25/1029 156/381 |
| 6,591,472 B1 * | 7/2003 | Noone | .............. | A61M 25/0009 264/171.13 |
| 6,740,273 B2 * | 5/2004 | Lee | ................... | A61M 25/1036 264/130 |

(Continued)

FOREIGN PATENT DOCUMENTS

| | | |
|---|---|---|
| EP | 0 841 072 A2 | 5/1998 |
| JP | 2008-183226 A | 8/2008 |

OTHER PUBLICATIONS

The extended European Search Report issued on Feb. 12, 2014, by the European Patent Office in corresponding European Patent Application No. 13193632.0-1506. (5 pages).

*Primary Examiner* — Gerald Landry, II
(74) *Attorney, Agent, or Firm* — Buchanan Ingersoll & Rooney PC

(57) ABSTRACT

A method of producing a catheter tube allows a plurality of catheter tubes to be continuously produced using a common core rod, with a proximal end connecting part efficiently attached. The method involves: forming a tubular body on the core rod including an inner layer covering body and an outer layer covering body; attaching a proximal end connecting part, forming a cylindrically shaped hub to a proximal end of the catheter tube, to a radially outer side of the inner layer covering body and the outer layer covering body; severing a tubular continuous body obtained on the core rod is severed at a given position after the proximal end connecting part is attached to produce a plurality of single tubes, each of which is provided with one of the hubs; and removing the core rod from the single tube.

7 Claims, 6 Drawing Sheets

(56) References Cited

U.S. PATENT DOCUMENTS

| | | | |
|---|---|---|---|
| 2005/0137576 A1* | 6/2005 | Packard | A61M 25/001 604/524 |
| 2005/0214492 A1* | 9/2005 | Zhong | A61L 29/085 428/36.91 |
| 2007/0240817 A1* | 10/2007 | Strong | A61M 25/0009 156/304.3 |
| 2009/0240235 A1* | 9/2009 | Murata | A61M 25/001 604/527 |
| 2010/0145313 A1* | 6/2010 | Packard | A61M 25/0012 604/535 |
| 2010/0256603 A1* | 10/2010 | Lippert | A61M 25/0009 604/524 |
| 2010/0268192 A1* | 10/2010 | El-Hibri | A61L 29/06 604/511 |
| 2011/0125134 A1* | 5/2011 | Schwager | A61L 24/046 604/533 |
| 2011/0264056 A1* | 10/2011 | Parker | A61F 2/95 604/264 |
| 2012/0016344 A1* | 1/2012 | Kusakabe | A61M 25/0021 604/528 |

* cited by examiner

METHOD OF PRODUCING CATHETER TUBE AND CONTINUOUS BODY OF THE SAME

CROSS REFERENCES TO RELATED APPLICATIONS

This application claims priority to Japanese Application No. 2012-254638 filed on Nov. 20, 2012, the entire content of which is incorporated herein by reference.

TECHNICAL FIELD

The present invention relates to a method of producing a catheter tube and a continuous body of a catheter tube which is used for a catheter configured to be positioned in a lumen such as a blood vessel or a body cavity.

BACKGROUND DISCUSSION

In recent years, treatment of a lumen such as a blood vessel or a body cavity using a catheter has been performed frequently since such a treatment has very low surgical stress. For example, a catheter which is selectively introduced into a complicatedly branched blood vessel in the body is, generally, selectively pushed in to the blood vessel along a guide wire that is previously introduced into the blood vessel. A medicine for treatment, a contrast medium for diagnosis, or the like is accordingly transferred from the operator side (proximal end side) to a distal end side. Therefore, an elongated catheter tube constituting the catheter has large inner and outer diameters in the proximal end side which enhances sufficient stiffness to provide sufficient pushability and also provides injection characteristics of a medicine or a contrast medium. Also, the elongated catheter tube has smaller inner and outer diameters on the distal end side than those on the proximal end side, which gives flexibility to improve accessibility to a peripheral blood vessel and followability to the guide wire.

An example of a method of producing such a catheter tube is described in Japanese Patent Application Laid-Open No. 2008-183226. In this method, a thermoplastic resin is coated and formed on a core rod which is constituted with thick portions and thin portions continuously aligned with a given space in between. A plurality of catheter tubes is formed as a continuous body on the same core rod. The continuous body is severed together with the core rod into individual catheter tubes. The core rod is then removed by pulling-out the rod, thus producing the catheter tube.

A hub (proximal end connecting part) which functions as an insert port into a lumen for a guide wire, an injection port into a lumen for a liquid medicine, an embolus material, a contrast medium, or the like, and a gripping part used to operate a catheter tube, may be connected to a proximal end portion of the catheter tube. However, there is no discussion about a hub in Japanese Patent Application Laid-Open No. 2008-183226 mentioned above, which means that a hub needs to be installed to each catheter tube after each catheter tube is severed from a continuous body constituted of a plurality of catheter tubes.

SUMMARY

The disclosure here describes a method of producing a catheter tube, in which a plurality of catheter tubes are continuously produced using a common core rod and with a proximal end connecting part efficiently installed, and also describes a continuous body of a catheter tube.

A method of producing a catheter tube configured as described above involves the covering body being coated on the core rod, and then the proximal end connecting part is attached with a given space, and further then the tubular continuous body obtained on the core rod is severed at a given position into a plurality of single tubes, each of which is provided with a proximal end connecting part. Therefore, it is not necessary to reposition the already severed single tube to attach the proximal end connecting part on the tube, thereby reducing the number of repetitions of positioning for the operation. Consequently, a plurality of catheter tubes is continuously and simultaneously produced using the same core rod, thereby enabling efficient production of the catheter tube.

According to another aspect disclosed here, a method of producing catheter tubes each possessing a distal end portion and a proximal end portion at which is fixed a hub comprises: coating a core rod with resin to form a covering body overlying the core rod, the covering body possessing an axial extent; attaching a plurality of cylindrically shaped proximal end connecting parts to a radially outer side of the covering body such that a space exists between the radially outer side of the covering body and an inner side of each of the cylindrically shaped proximal end connecting parts facing toward the covering body; with the cylindrically shaped proximal end connecting parts being attached to the radially outer side of the covering body so that the cylindrically shaped proximal end connecting parts are axially spaced apart from one another along the axial extent of the covering body; severing the core rod and the covering body at a plurality of axially spaced apart locations after attaching the cylindrically shaped proximal end connecting part to the radially outer side of the covering body to sever the core rod coated with the resin into a plurality of separated sections which each include a portion of the core rod covered by a portion of the covering body and one of the proximal end connecting parts attached to the radially outer side of the portion of the covering body; and removing the core rod from each of the sections to result in the catheter tubes in which the proximal end connecting part is the hub which is fixed to the proximal end portion of the catheter tube.

When a shape transferring step in which a shape corresponding to a shape of an end portion of the catheter tube is transferred with a given space to the covering body is further included before the proximal end connecting part attaching step, the shape of the portion to which a proximal end connecting part is attached is transferred before a proximal end connecting part is attached, thereby enabling further efficient production of the catheter tube.

The core rod is preferably previously formed so as that the thick portion and the thin portion, each having a different diameter, are continuously arranged with a given space in between, so that a catheter tube having a different diameter at the distal end portion and the proximal end portion can efficiently be produced using a tubular continuous body which is continuously lined.

The covering body can be produced by coating an inner layer covering body on the core rod so as to be in contact with the core rod, and coating resin forming an outer layer covering body on the radially outer side of the inner layer covering body. The proximal end connecting part can this be efficiently attached to the catheter tube having a multilayer structure.

When a reinforcement body forming step in which a reinforcement body configured with a wire is formed so as to be in contact with the covering body is further included before the proximal end connecting part attaching step, the catheter tube to be produced can be locally reinforced as desired, thereby improving pushability and kink resistance.

According to another aspect, a continuous body of a catheter tube in which a plurality of intermediate bodies of a catheter tube, that is a plurality of single tubes, are continuously formed on the same core rod. The continuous body of a catheter tube includes a core rod, a covering body which is formed on the core rod by coating a resin on the core rod, and a cylindrically shaped proximal end connecting part, which is to be connected to the proximal end of the catheter tube, attached to the radially outer side of the covering body with a given space along the axial direction of the core rod. The continuous body of the catheter tube already has a proximal end connecting part attached to the continuous body at predetermined spaced apart intervals before being severed. Therefore, it is not necessary to reposition the single tube after being severed to attach the proximal end connecting part to the single tube, thereby reducing the number of repeated positionings of the tube for carrying out working operations, and thus enabling efficient production of the catheter tube.

When the core rod provided on the continuous body is formed so as to have a thick portion and a thin portion, each having a different outer diameter, continuously arranged with a given space in between, a catheter tube having a different diameter at a distal end portion and a proximal end portion can efficiently be produced using a continuously lined continuous body.

When the covering body provided on the continuous body includes an inner layer covering body formed by coating a resin on the core rod so as to be in contact therewith and an outer layer covering body formed by coating a resin in the radially outer side of the inner layer covering body, a catheter tube having a multilayer structure with a proximal end connecting part attached thereon can efficiently be produced using a continuously lined continuous body.

When the continuous body further has a reinforcement body, configured with a wire in contact with the covering body, the catheter tube to be produced can be locally reinforced as desired, thereby improving pushability and kink resistance.

BRIEF DESCRIPTION OF THE DRAWINGS

FIGS. 3(A)-3(F) are schematic views explaining aspects of a method of producing a catheter tube according to an embodiment disclosed by way of example in a sequence of steps in which FIG. 3(A) is a core rod preparing step, FIG. 3(B) is an inner layer covering body forming step, FIG. 3(C) is a reinforcement body forming step, FIG. 3(D) is a reinforcement body removing step, FIG. 3(E) is a marker arranging step, and FIG. 3F is an outer layer covering body forming step.

FIGS. 4(A)-4(E) are schematic views explaining other aspects of a method of producing a catheter tube according to an embodiment disclosed here by way of example in a sequence of steps in which FIG. 4(A) is a shape transferring step, FIG. 4(B) is a hydrophilic covering body forming step, FIG. 4(C) is a proximal end connecting part attaching step, FIG. 4(D) is a severing step, and FIG. 4(E) is a core rod drawing step and a core rod removing step.

DETAILED DESCRIPTION

Figure 1:
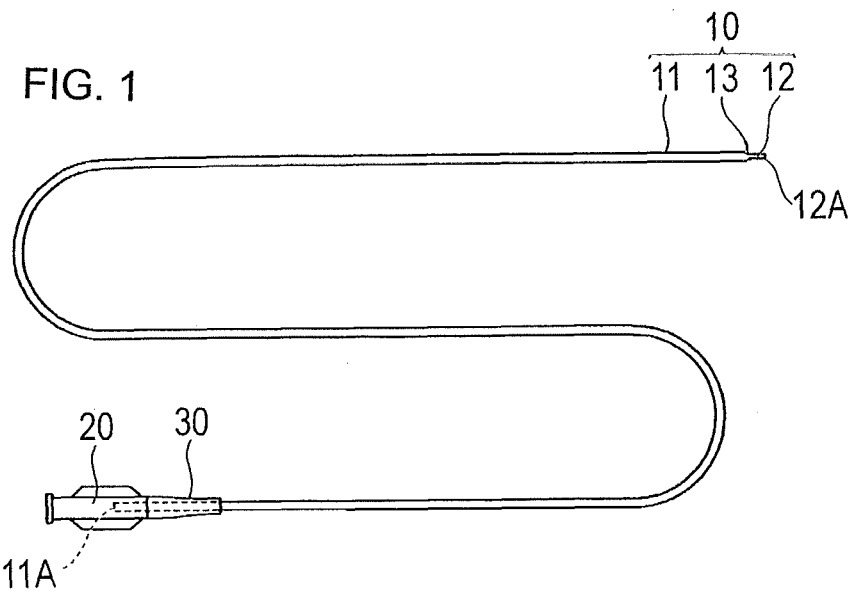
FIG. 1 is a plan view illustrating a catheter.

Set forth below is a detailed description of a continuous body of a catheter tube and a method of producing a catheter tube disclosed here. The ratio of dimensions in the drawings may be magnified for the convenience of explanation, and therefore differ from the actual ratio.

A catheter tube 10 produced by a method of producing a catheter tube according to an embodiment disclosed here is illustrated in FIG. 1 and is used as a catheter 1 to be inserted into a blood vessel, a bile duct, a trachea, an esophagus, a urethra, or other living lumens and body cavities for curing, diagnosis or the like. The catheter 1 includes an elongated catheter tube 10, a hub 20 (proximal end connecting part) which is connected to a proximal end of the catheter tube 10, and an anti-kink protector 30 (proximal end connecting part) provided at a portion connecting the catheter tube 10 and the hub 20. In the following description, and with reference to the drawing figures, a portion of the catheter to be inserted into a lumen is referred to as the "distal end" or the "distal end side", and a portion close to an operator is referred to as the "proximal end" or the "proximal end side".

Figure 2:
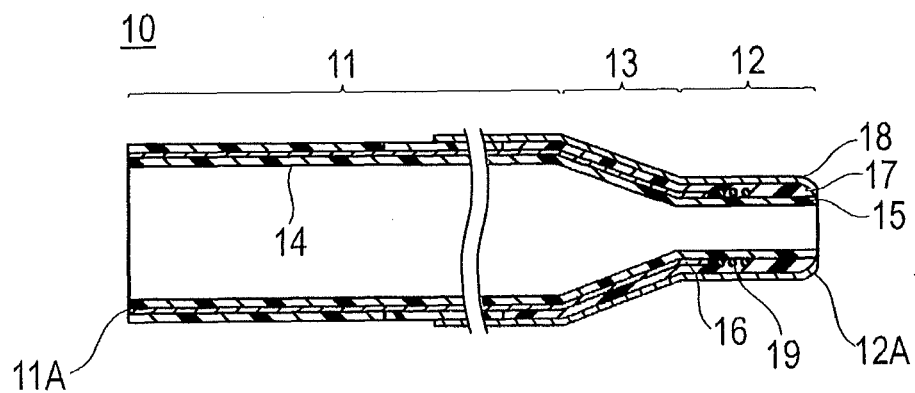
FIG. 2 is a cross-sectional view illustrating a catheter tube produced by a method of producing a catheter tube according to an embodiment disclosed here.

As illustrated in FIGS. 1 and 2, the catheter tube 10 is a flexible tubular component including a tube proximal end portion 11 having a given outer diameter and a given inner diameter, a tube distal end portion 12 having an outer diameter and an inner diameter each of which is smaller than that of the tube proximal end portion 11, and a tube transition portion 13 possessing an outer diameter and an inner diameter that gradually change along the axial direction between the tube proximal end portion 11 and the tube distal end portion 12. A lumen 14 is formed inside the catheter tube 10 through the proximal end to the distal end. The lumen 14 functions, for example, as a guide wire lumen in which a guide wire is inserted through the lumen when the catheter 1 is inserted into a living lumen. Further, the lumen 14 can be used as a passage for a liquid medicine, an embolus material, a contrast medium, and the like.

The catheter tube 10 is configured with a plurality of layers and includes an inner layer 15 constituting an innermost layer, a reinforcement layer 16 formed outside of the inner layer 15, an outer layer 17 formed in the outer side of the inner layer 15 and the reinforcement layer 16, a hydrophilic layer 18 coated on the outside of the outer layer 17, and a marker 19. The distal end side of the reinforcement layer 16 in the tube distal end portion 12 is removed to provide flexibility at the distal end side of the catheter tube 10. That is, the distal-most end of the reinforcement layer 16 is spaced proximally from the distal-most end of the catheter so that the distal end portion of the catheter is devoid of the reinforcement layer 16. A most distal end portion 12A is formed at the distal end side of the tube distal end portion 12 and a most proximal end portion 11A is formed at the proximal end side of the tube proximal end portion 11. The most distal end portion 12A of the tube distal end portion 12 is processed to have a curved R surface in order to minimize the impact on a living tissue when the catheter tube is inserted into a living lumen or a body cavity. That is, the distal-most end portion 12A of the tube distal end portion 12 is processed such as by chamfering so that the distal-most end portion 12A has a curved surface possessing a radius R. Instead of processing the R surface, processing to form a tapered surface may be applied. The configurations and materials of the inner layer 15, the reinforcement layer 16, the outer layer 17, and the hydrophilic layer 18 will be described below in detail in the description on a method of production.

As for the hub 20, the proximal end portion of the catheter tube 10 is fluid-tightly fixed using an adhesive, heat-sealing, a fastener, or the like. The hub 20 functions as an insert port to insert a guide wire into the lumen 14 and an injection port to inject a liquid medicine, an embolus material, a contrast medium, and the like into the lumen 14. The hub 20 further functions as a gripping part when the catheter 1 is operated. Though not specifically limited in this regard, the material of the hub 20 may preferably be a thermoplastic resin such as polycarbonate, polyamide, polysulfone, polyarylate, or methacrylate-butylene-styrene copolymer.

The anti-kink protector 30 is formed of a flexible material provided to encircle the circumference of the catheter tube 10, and restrains kinking of the catheter tube 10 at the portion where the catheter tube 10 and the hub 20 are connected. As for materials of the anti-kink protector 30, for example, natural rubber, silicone resin, or the like may preferably be used.

A method of producing a catheter tube 10 according to an embodiment disclosed as an example will be next described. The catheter tube 10 manufacturing method includes a core rod preparing step (see FIG. 3(A)) for preparing an elongated core rod 40, an inner layer covering body forming step (covering body forming step) (see FIG. 3(B)) in which an inner layer covering body 51 (covering body or cover) is formed on or coated on the core rod 40, a reinforcement body forming step (see FIG. 3(C)) in which a reinforcement body 52 is formed on the inner layer covering body 51, a reinforcement body removing step (see FIG. 3(D)) in which a portion of the reinforcement body 52 is removed, a marker arranging step (see FIG. 3(E)) in which the marker 19 is arranged on the reinforcement body 52, an outer layer covering body forming step (covering body forming step) (see FIG. 3F) in which an outer layer covering body 53 (covering body or cover) is formed by integrally coating the reinforcement body 52 and the inner layer covering body 51, a shape transferring step (see FIG. 4(A)) in which each shape of the most distal end portion 12A and the most proximal end portion 11A is transferred to the catheter tube 10, a hydrophilic covering body forming step (see FIG. 4(B)) in which a hydrophilic covering body 54 is coated, a proximal end connecting part attaching step (see FIG. 4(C)) in which the hub 20 (proximal end connecting part) is attached, a severing step (see FIG. 4(D)) in which a structure obtained on the core rod 40 is severed at a given position on the core rod 40 into plural single tubes or sections 61, a core rod drawing step (see FIG. 4(E)) for drawing the core rod 40, and a core rod removing step (see FIG. 4(E)) for removing the core rod 40 from each of the single tubes 61. The inner layer covering body 51, the reinforcement body 52, the outer layer covering body 53, and the hydrophilic covering body 54 which are formed on the core rod 40 consequently become the inner layer 15, the reinforcement layer 16, the outer layer 17, and the hydrophilic layer 18 of the catheter tube 10, respectively.

Figure 3:
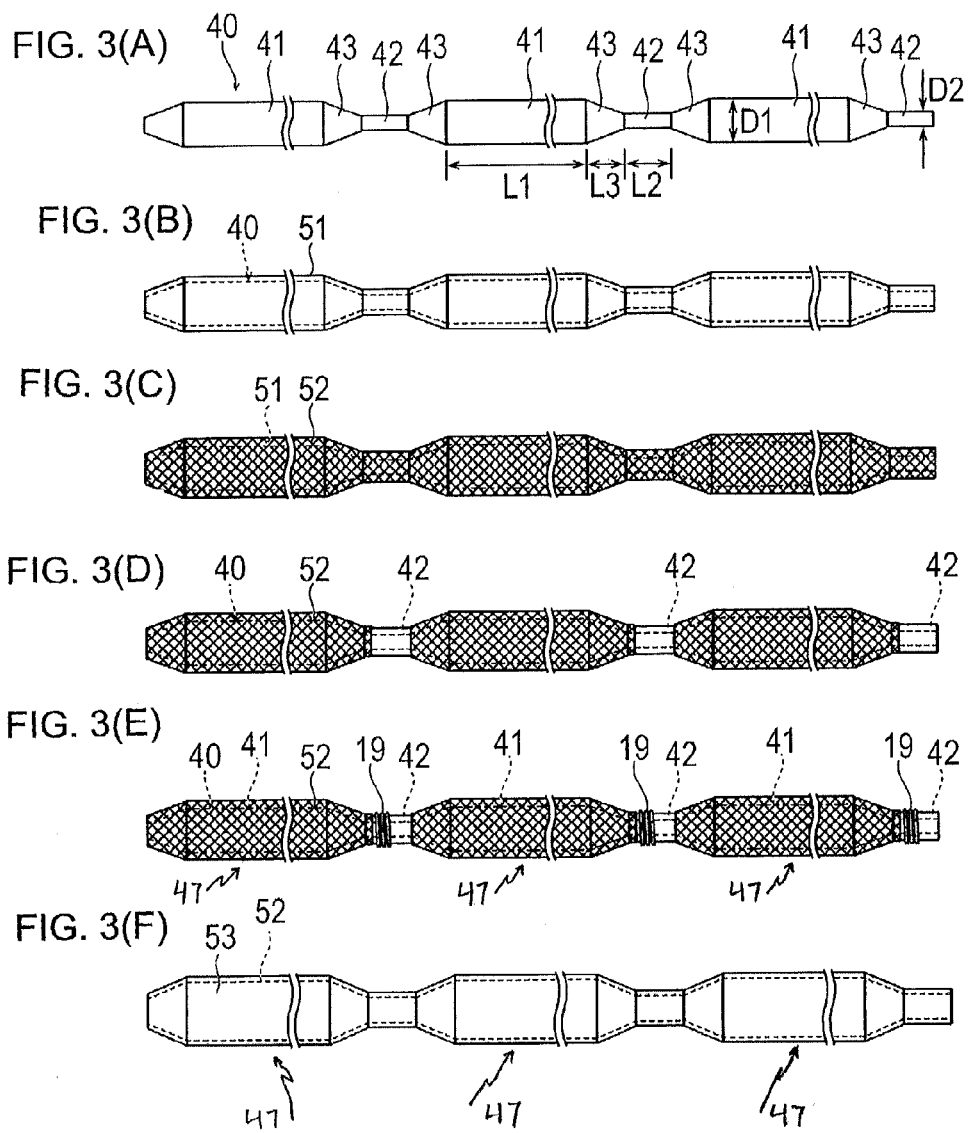

In the core rod preparing step illustrated in FIG. 3(A), the core rod 40 is processed to have a relatively thicker portion (referred to as the thick portion) 41, a relatively thinner portion (referred to as the thin portion) 42, and a transition portion 43 (at which the thick portion 41 and the thin portion 42 transition to one another) by machining such as cutting, polishing, grinding, forging, welding, elongation drawing using a split die, or by chemical machining such as etching. Alternatively, in the core rod preparing step, the core rod 40 may be prepared by purchasing a core rod 40 already processed as described above.

The core rod 40 prepared for the core rod preparing step is configured with the thick portion 41 having a given outer diameter, the thin portion 42 having an outer diameter smaller than that of the thick portion 41, and a transition portion 43 having an outer diameter gradually changing along the axial direction of the core rod 40 between the thick portion 41 and the thin portion 42. A plurality of the thick portions 41, the thin portions 42, and the transition portions 43 alternate with one another as illustrated and are aligned to constitute the core rod 40. A ratio D1/D2, which is a ratio of the outer diameter D1 of the thick portion 41 to the outer diameter D2 of the thin portion 42, is preferably larger than 1.00 and as large as 1.31 or smaller, more preferably as large as 1.30 or smaller, and even more preferably as large as 1.22 or smaller. The ratio D1/D2 is larger than 1. Since the ratio D1/D2 is 1.31 or smaller, not only the thin portion 42 but also the thick portion 41 is favorably drawn in the core rod drawing step so as to prevent only the thin portion 42 from being thinned. Thereby, the core rod 40 can favorably be removed in the core rod removing step and a catheter tube 10 which is sustainable under practical use can be produced. The ratio D1/D2 of 1.22 or smaller more reliably prevents a situation in which only the thin portion 42 is thinned in the core rod removing step so that the core rod 40 can more reliably be removed in the core rod removing step, thereby enabling production of a more favorable catheter tube 10.

As an example, the length L1 of the thick portion 41 may be 1800 mm, the length L2 of the thin portion 42 may be 150 mm, the length L3 of the transition portion 43 may be 50 mm, the outer diameter D1 of the thick portion 41 may be 0.55 to 0.6 mm, and the outer diameter D2 of the thin portion 42 may be 0.45 to 0.50 mm. The dimensions, however, are not limited to these values.

As a material of the core rod 40, a ductile metal such as a copper wire and a soft stainless steel wire, or a resin strand such as polyamide (PA) may be used. The cross-sectional shape of the core rod 40 is not limited to a circle and may be any shape such as an oval, a half circle, and a polygon. Such core rod 40 can easily be prepared in such a manner like purchasing.

After the core rod preparing step, the inner layer covering body 51 is formed on the core rod 40 as illustrated in FIG. 3(B) (inner layer covering body forming step). The inner layer covering body 51 produced in this step is the inner layer 15 in the finished catheter tube or catheter. As a material of the inner layer covering body 51, a thermoplastic resin, a thermosetting resin, or the like may be applied, and a low friction material such as a fluorine-based resin and high density polyethylene (HDPE) is preferable.

A material exhibiting radiopacity (radiopaque material) may be mixed with the inner layer covering body 51. When the inner layer covering body 51 is formed of a low friction material such as a fluorine-based resin, the outer surface of the inner layer covering body 51 may preferably be processed with a roughening treatment by chemical etching or the like so that other material can be applied to coat the outside of the inner layer covering body 51.

When a thermoplastic resin is used as a material of the inner layer covering body 51, the inner layer covering body 51 can be formed by extrusion molding at a given molding temperature (die temperature) and a given take-up speed using an extrusion molding machine. In this manner, an extrusion molded body (inner layer covering body 51) having an almost uniform thickness can be obtained. As an example, the outer diameter of the inner layer covering body 51 at the portion corresponding to the thick portion 41 can be set to 0.57 to 0.76 mm and the outer diameter of the inner layer covering body 51 at the portion corresponding to the thin portion 42 can be set to 0.47 to 0.53 mm, though the dimensions are not limited to these values. By adjusting the take-up speed, the thickness can be varied according to the portions.

Figure 5:
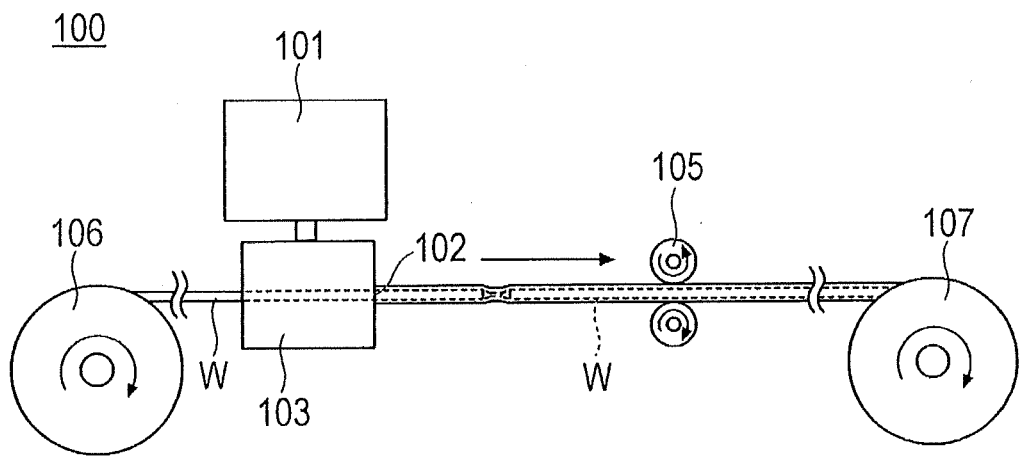
FIG. 5 is a schematic view explaining a method of forming a layer by extrusion molding.

The method of extrusion molding will now be briefly described. A layer of thermoplastic resin (inner layer covering body 51 in the embodiment) is formed on a core material W (core rod 40 in the embodiment) using a typical extrusion molding machine 100 such as shown in FIG. 5. The extrusion molding machine 100 includes an extrusion machine 101 which extrudes a heat-melted material, a die 103 which extrudes the resin extruded from the extrusion machine 101 from an extrusion port 102, a take-up machine 105 which takes up the core material W that penetrates through the die 103 and is positioned in the center of the extrusion port 102, a supply roll 106, around which the core material W is wound to be supported and supplies the core material W to the die 103, and a recovering roll 107 which recovers the extrusion molded core material W. A material is extrusion molded on the core material W by supplying a heat-melted material to the die 103 with the extrusion machine 101, continuously supplying the material on the core material W from the extrusion port 102 while taking up the core material W, supplied from the supply roll 106 and positioned at the extrusion port 102, with the take-up machine 105, and thereby coating the core material W with the material. The core material W coated with the material is wound around the recovering roll 107 to be recovered after the coated material is solidified. By varying the take-up speed of the take-up machine 105, the outer diameter of the extrusion molded product can optionally be changed. If the core material W is directly received from the previous step and the core material W coated with thermoplastic resin is directly transferred to the next step, it is not necessary to provide the supply roll 106 and the recovering roll 107. Further, when a fluorine-based resin (e.g., PTFE) is used as a resin for the extrusion molding of the inner layer covering body 51, such a material in which a fluorine-based resin lubricant is mixed as an additive with a resin powder can be extruded.

Figure 6:
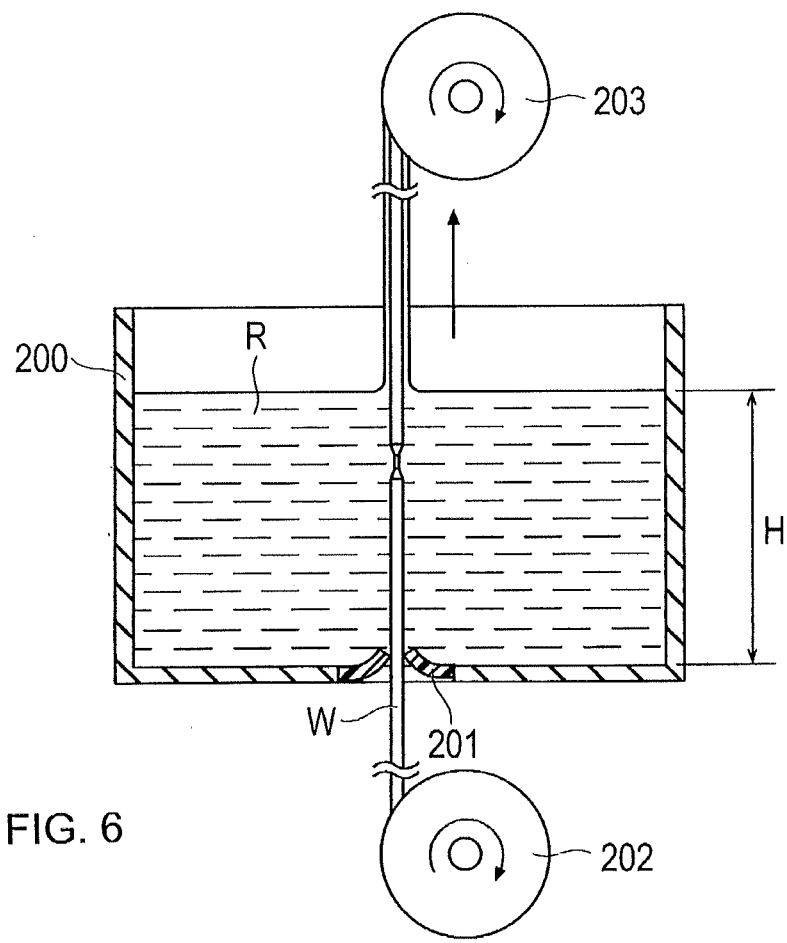
FIG. 6 is a schematic view explaining a method of forming a layer by dip forming.

In the inner layer covering body forming step, the inner layer covering body 51 can be formed, as an alternative to extrusion molding, by dip forming. The method of dip forming will now be briefly described. First, a solution R in which a material or a resin is dissolved in a solvent, or a dispersion R in which a material or a resin is dispersed in a diluent, is contained in a container 200 as illustrated in FIG. 6. The core material W (core rod 40 in the embodiment) is supplied from the supply roll 202 around which the core material W is wound to be supported. The supplied core material W is inserted in or introduced into the container 200 from below through a flexible valve 201, capable of keeping fluid tightness while being penetrated by the core material W, provided on the bottom of the container 200. The core material W is pulled up out of the container 200 after being dipped (immersed) in the solution R or the dispersion R in the container 200. In this manner, the solution R or the dispersion R adheres to the outer circumference surface of the core material W. Then the solution R or the dispersion R adhering to the core material W is dried by heating with hot air, a heater, or the like, and further sintered when a dispersion R of fluorine-based resin or the like is used, thereby forming the inner layer covering body 51. The core material W coated with the material is wound around the recovering roll 203 to be recovered after the coated material is solidified. Conventional types for the solution and the diluent can be applied. By changing the speed of pulling up from the container 200, the layer thickness of the solution R or the dispersion R adhering to the core material W can optionally be changed so that the thickness of the inner layer covering body 51 can optionally be changed. The layer thickness is determined by mutual effects among the density, the surface tension, and the viscosity of the solution R or the dispersion R, the gravity force acting thereon, and the pull-up speed of the core material W. When the pull-up speed from the container 200 is decreased, the layer thickness of the solution R or the dispersion R adhering to the core material W can be increased. When the pull-up speed from the container 200 is increased, the layer thickness of the solution R or the dispersion R adhering to the core material W can be decreased. For example, by making the layer thickness of the portion corresponding to the thin portion 42 thinner than that of the thick portion 41, the layer thickness of the portion corresponding to the transition portion 43 can be gradually changed.

Further, when the viscosity of the solution R or the dispersion R is high, the thickness of the coating tends to be non-uniform. In such a case, the coating thickness can be precisely controlled by providing a viscosity low enough to obtain a uniform coating layer thickness and repeating dip forming a plurality of times, thereby gradually increasing the coating layer thickness. The dip forming can be repeated by moving the recovering roll 203 by which the core material W coated with the material is recovered beneath the container 200 so that the recovering roll 203 can be used as a supply roll 202 to carry out the dip forming again. When the dip forming is repeatedly carried out, it is preferable to dry and sinter the solution R or the dispersion R by heating with hot air, a heater, or the like in each dip forming operation.

Further when the dip forming is repeatedly carried out, it is preferable to carry out the dip forming by pulling up the core rod 40 in an opposite direction at least once, instead of carrying out every dip forming in the same direction. It is more preferable to change the direction of the dip forming after each dip forming. By carrying out the dip forming in the opposite direction at least once, the nonuniformity of the layer thickness depending on the pull-up direction can be restrained, thereby providing a uniform layer thickness. By changing the direction of the dip forming after each dip forming, the nonuniformity of the layer thickness depending on the pull-up direction is minimally restrained, thereby providing a better uniform layer thickness. In particular, for a core rod 40 with a varying outer diameter, the nonuniformity of the layer thickness depending on the pull-up direction is likely to occur in the portion where the outer diameter changes. Therefore, it is highly effective to carry out, at least once, the dip forming in the opposite direction for forming a uniform layer thickness when the dip forming is applied to the core rod 40 in which the thick portion 41 and the thin portion 42 are formed.

Drying and sintering can be carried out for each dip forming. However, drying and sintering can also be carried out after continuously conducting plural times of dip forming without drying and sintering between each dip forming. By continuously conducting plural times of dip forming without drying and sintering between each dip forming, a thickness can be precisely controlled for each desired portion.

Further, during the repetition of the dip forming, the number of repetitions in a certain portion of the core rod 40 can be changed. An example of such method is described below. When a large number of repetitions is desired for a certain portion, the portion is pulled up to dry and sinter the solution R or the dispersion R which is coated on the portion, and then the core rod 40 which is in a pulled up position is moved downward to dip the portion in which a large number of repetitions is desired in the solution R or the dispersion R. Then the core rod 40 is moved upward again so that the portion in which a large number of repetitions is desired can be pulled up again so as to be further coated with the solution R or the dispersion R. By repeating this process, a desired number of repetitions of the dip forming can be carried out for a certain portion of the core rod. In this manner, by changing the moving direction of the core rod 40, the number of repetitions of the dip forming can suitably be determined for a certain portion. Therefore, for example, the number of dip forming repetitions can be determined so that the relationship amongst each of the portions is as follows: transition portion>thick portion>thin portion; or thick portion>transition portion>thin portion. In these expressions of the relationships, A>B means that the number of repetitions for A is larger than the number of repetitions for B. It is preferable to carry out the dip forming so as that the number of repetitions in the transition portion is the largest, which can give a gradual change in the thickness of the transition portion. The transition portion 43 of the core rod 40, before being coated with the inner layer covering body, has a tapering outer shape or sloping outer surface. This tapering outer shape or sloping outer surface of the transitions section can be changed slightly or fine-tuned by virtue of the dip forming repetitions relationships described above so that the thickness of the inner layer covering body in the transition section gradually changes. Also in this method, drying and sintering can be carried out following each dip forming. However, drying and sintering may be carried out after continuously conducting plural times of dip forming without drying and sintering following each dip forming.

Further, instead of moving the core rod 40, the fluid volume H of the solution R or the dispersion R, as illustrated in FIG. 6, can be changed to vary the depth so that the pull-up location, the pull-up speed, and the pull-up direction (upward or downward) can be adjusted.

Further, when the core material W is pulled up from the container 200 with the core material W rotating about its central axis, the centrifugal force acts on the solution R or the dispersion R coated on the core material W, by which the volume of coating can optionally be changed. That is, the greater rotational speed of the core material W produces the greater centrifugal force acting on the core material W, thereby decreasing the layer thickness of the solution R or the dispersion R coated on the core material W. The smaller rotational speed of the core material W produces the smaller centrifugal force acting on the core material W, thereby increasing the layer thickness of the solution R or the dispersion R coated on the core material W. For example, when the rotational speed during the pull-up of the thin portion 42 is greater than the rotational speed during the pull-up of the thick portion 41, the thickness of the layer which coats the thin portion 42 is smaller than the thickness of the layer which coats the thick portion 41. Further, by gradually changing the rotational speed of the core rod 40 during the pull-up of the transition portion 43, the layer thickness of the transition portion 43 can be changed in a smoothly sloping manner between the thick portion 41 and the thin portion 42. Thereby, the distal end side of the produced catheter tube 10 can be made more flexible than the proximal end side of the produced catheter tube 10. Further, regarding that the centrifugal force acting on the core rod 40 is greater as the outer diameter of the core rod 40 is larger, the rotational speed may be adjusted in the portion in which the outer diameter varies so as to provide a uniform layer thickness of the solution R or the dispersion R which is to be coated.

In this embodiment, since the core material W is provided from the supply roll 202 and recovered by the recovering roll 203, it is preferable to rotate the supply roll 202 and the recovering roll 203 about the central axis of the core material W in the container 200. However, the configuration of the apparatus is not limited to the core material W in the container 200 being rotated.

Further, in the case when a mixture such as a particle or a fiber is mixed in the solution R or the dispersion R during a pull-up of the core material W from the container 200 with the core material W rotating, the fibers can be oriented in the same direction as the pull-up direction in which the core material W is pulled-up.

In the case when the dip forming with rotation is repeated plural times, it is preferable to carry out the dip forming while rotating the core rod 40 in the opposite direction at least once instead of rotating the core rod 40 in the same direction every time. It is more preferable to carry out the dip forming reversing the direction of rotation after each dip forming. By carrying out the dip forming with a rotation in the opposite direction at least once, the nonuniformity of the layer thickness depending on the rotational direction is restrained, thereby providing a uniform layer thickness. By carrying out the dip forming while changing the direction of rotation after each dip forming, the nonuniformity of the layer thickness depending on the rotational direction is minimally restrained, thereby providing a better uniform layer thickness.

In the case when the layer thickness of the solution R or the dispersion R which coats the core material W is to be decreased by controlling the pull-up speed, it is necessary to reduce the pull-up speed. The viscosity of the solution R or the dispersion R is relatively low, and so with a relatively slow pulling rate, R is gradually dropped by gravity, thus reducing the film thickness. However, when the rotational speed of the core material W is controlled as described above, the rotational speed can be increased to control the layer thickness without reducing the pull-up speed, thereby enabling reduction of the production time.

As described above, by adjusting the viscosity of the solution R or the dispersion R, the pull-up speed, the pull-up direction, the portion to be pulled up, the fluid volume of the solution R or the dispersion R (depth in the container 200), the number of repetitions of the dip forming, the rotational speed, and the direction of rotation, the coating thickness and the production time of the coating inner layer covering body 51 to be coated can be precisely controlled.

If the inner layer covering body 51 can be dip formed, it is not necessary for the container 200 to be in the form described above. For example, instead of penetration of the core material W into the container 200 from the bottom of the container 200, the core material W may be dipped (immersed) in or introduced into the solution R or the dispersion R from above the container, and then bent to be pulled upward again. Further, after adhering the solution R or the dispersion R to the outer circumference surface of the core material W, the outer diameter of the inner layer covering body 51 can be adjusted by restricting the amount of the adhering solution R or the dispersion R by passing the core material W through a die having a given inner diameter. Further, when the core material W is directly received from the previous step and the core material W coated with the material is directly transferred to the next step, it is not necessary to provide the supply roll 202 and the recovering roll 203 around which the core material W is wound.

Further, the method of forming the inner layer covering body 51 in the inner layer covering body forming step is not limited to the extrusion molding or the dip forming. For example, the inner layer covering body 51 may be formed by adhering a solution in which a resin is dissolved in a solvent, or a dispersion in which a resin is dispersed in a diluent, to the core rod 40 by a well known method such as spraying (spray), application, and printing, and then drying, and sintering for a certain material, the solution or the dispersion adhering to the core rod 40 by heating with hot air, a heater, or the like.

After the inner layer covering body forming step, the reinforcement body 52 is formed so as to coat at least a portion of the inner layer covering body 51 as illustrated in FIG. 3(C) (reinforcement body forming step). The reinforcement body 52 produced in this step is the reinforcement layer 16 in the finished catheter tube or catheter.

The reinforcement body 52 is formed by a wire continuously wound around the outwardly facing surface of the inner layer covering body 51. The wire can be continuously wound around the inner layer covering body 51 in the form of a braid with a given grid interval. Regarding the reinforcement body 52, the wire may be laterally wound in a common direction, or wound in various directions such as a right-handed direction or a left-handed direction. Also, a winding pitch, a grid interval, an inclination angle to the circumferential direction, or the like may be changed among locations. The configuration is not limited.

A metal wire such as platinum (Pt) and tungsten (W), a resin fiber, a carbon fiber, a glass fiber, or the like may be applied as a wire used for the reinforcement body 52, and some of these metal wires and fibers may be used together.

After the reinforcement body forming step, a portion of the reinforcement body 52 corresponding to the thin portion 42 is removed as illustrated in FIG. 3(D) (reinforcement body removing step). The portions to be removed are determined so that the removed portions are spaced apart and so that a given space exists between successive removed portions, with the removed portions corresponding to the distal end side of the tube distal end portion 12, to which flexibility is to be provided, of the plurality of catheter tubes 10 which are finally to be produced. The reinforcement body 52 can be removed by an electrochemical treatment using electrolysis, a chemical treatment using chemicals such as acids, a mechanical process using a cutter or the like, or an optical processing using a laser. Not only the portion corresponding to the distal end side of the tube distal end portion 12 of the plurality of catheter tubes 10 which is finally to be produced but also other portions may be removed.

After the reinforcement body forming step, a marker 19 having radiopacity is arranged on the inner layer covering body 51 as illustrated in FIG. 3(E) (marker arranging step).

The marker 19 produced in this step is the marker 19 in the finished catheter tube or catheter. The marker 19 is arranged in a manner that a wire formed of a material including a radiopacity material is wound around the portions corresponding to the thin portions 42 (at which the reinforcement body 52 has been removed) from the radially outer side of the core rod 40. The marker 19 is arranged from the radially outer side of the core rod 40, which is easy even when the subject to which the marker 19 is attached has a continuously lined form before being severed. As a material of the marker 19, a material produced by kneading an X-ray contrast medium such as a coupling compound of platinum, gold, silver, tungsten, a metal powder of alloys of platinum, gold, and silver, and tungsten, barium sulfate, and oxidation bismuth may be applied. The outer diameter of the wire constituting the marker 19 is, for example, about 30 to 50 µm, though not particularly limited as long as the wire has radiopacity.

In the illustrated embodiment, only one marker 19 is provided at each of the portions corresponding to the thin portions 42, though a plurality of markers 19 may be provided at each thin portion 42. Further, instead of providing the marker 19 at the portions corresponding to the thin portions 42, a marker or a plurality of markers may be provided to the portions corresponding to the thick portions 41. Further, the marker may be provided to both the thin portions 42 and the thick portions 41. By providing a plurality of markers, not only the location can be observed by X-ray from outside the body, but also the length can be measured by using the marker as a scale.

After the marker arranging step, the outer layer covering body 53 is formed on or applied to the outer surface of the structure formed on each unit core rod 47, coating at least a portion of the marker 19 and the reinforcement body 52 as illustrated in FIG. 3F (outer layer covering body forming step). The outer layer covering body 53 produced in this step is the outer layer 17 in the finished catheter tube or catheter. As an example, the outer diameter of the outer layer covering body 53 in the portion corresponding to the thick portion 41 may be 0.8 mm to 1.1 mm, and the outer diameter of the outer layer covering body 53 in the portion corresponding to the thin portion 42 may be 0.6 mm to 1.0 mm. The outer diameter of the outer layer covering body 53 in the portion corresponding to the transition portion 43 gradually changes in a range between 0.6 mm and 1.1 mm. The dimensions are not limited to the values mentioned above.

As a material of the outer layer covering body 53, for example, a thermoplastic resin such as polymer materials including polyolefin (e.g., polyethylene, polypropylene, polybutene, ethylene-propylene copolymer, ethylene-vinyl acetate copolymer, ionomer, or a mixture of two or more of the materials mentioned above), polyvinyl chloride, polyamide, polyester elastomer, polyamide elastomer, polyurethane, polyurethane elastomer, polyimide, and fluoric resin, or a mixture of the materials mentioned above, or a thermosetting resin such as epoxy resin may be applied. A radiopacity material may be mixed with the outer layer covering body 53.

In the outer layer covering body forming step, the outer layer covering body 53 can be extrusion molded using the extrusion molding machine 100 described above, as illustrated in FIG. 5, with the structure in which the unit core rod 47 is coated with the inner layer covering body 51 and the reinforcement body 52 (see FIG. 3(E)) used as the core material W.

Further, in the outer layer covering body forming step, the outer layer covering body 53 can be dip formed using the container 200 described above, as illustrated in FIG. 6, with the structure in which the core rod 40 is coated with the inner layer covering body 51 and the reinforcement body 52 (see FIG. 3(E)) used as the core material W.

Further, the method of forming the outer layer covering body 53 in the outer layer covering body forming step is not limited to the extrusion molding and the dip forming. For example, the outer layer covering body 53 may be formed by adhering a solution in which a resin is dissolved in a solvent, or a dispersion in which a resin is dispersed in a diluent, to the outer circumference surface of the inner layer covering body 51 and the reinforcement body 52 by a well known method such as spraying (spray), application, and printing, and subsequently drying, and sintering for a certain material, the adhered solution or dispersion by heating with hot air, a heater, or the like.

Figure 4:
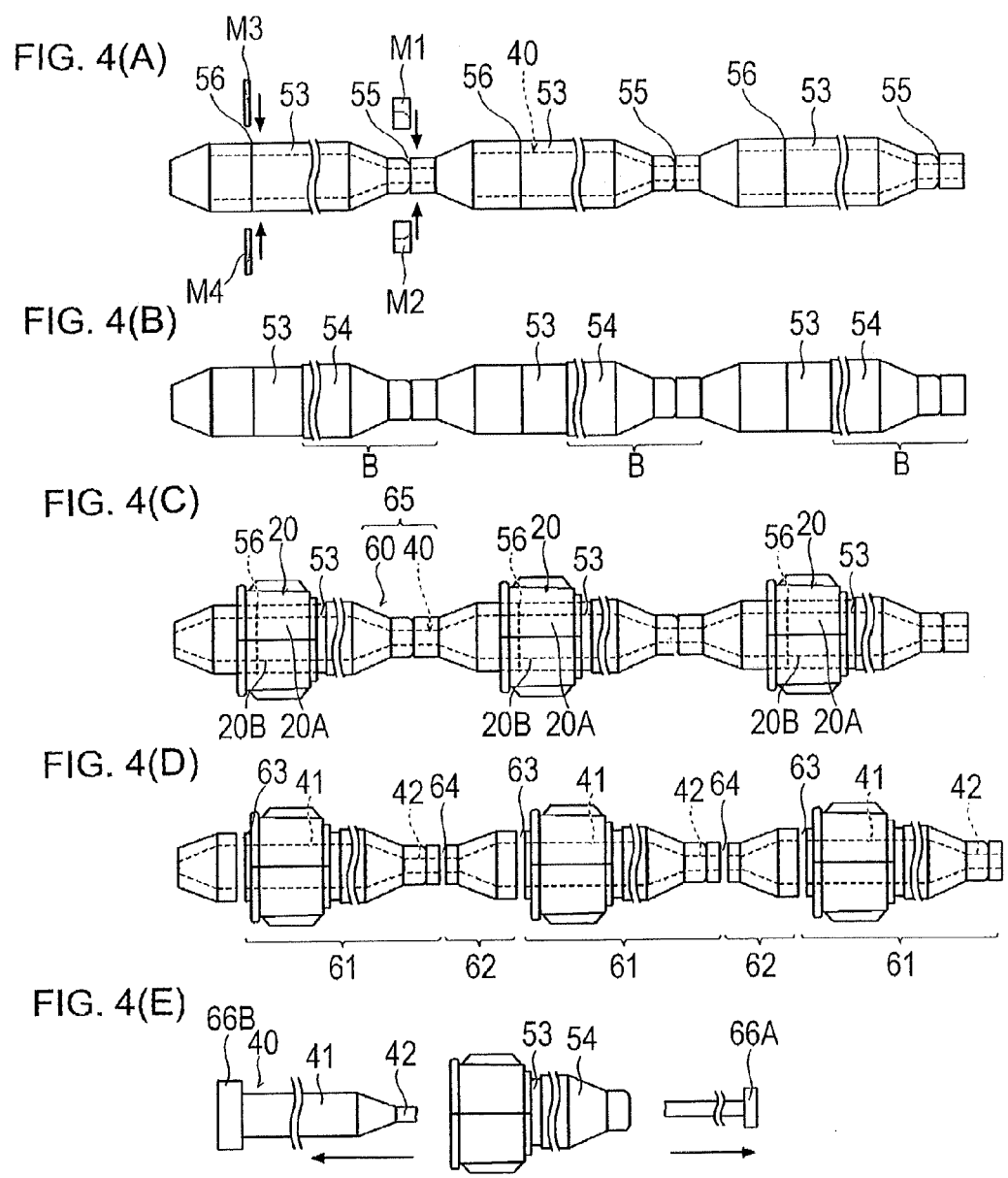

After the outer layer covering body forming step, the shapes corresponding to the most distal end portion 12A and the most proximal end portion 11A of the catheter tube 10 are transferred to the inner layer covering body 51 and the outer layer covering body 53 as illustrated in FIG. 4(A) (shape transferring step). To the shape transferred portion 55 corresponding to the most distal end portion 12A of the inner layer covering body 51 and the outer layer covering body 53, the shape with a curved surface similar to the shape of the most distal end portion 12A is transferred by an upper die M1 and a lower die M2 provided with a cavity corresponding to the shape of the curved surface at the most distal end portion 12A. It is preferable that the inner layer covering body 51 and the outer layer covering body 53 are severed to be completely split in the transverse direction (perpendicular to the central axis of the core rod 40) at the shape transferred portion 55 by the upper die M1 and the lower die M2 reaching the core rod 40, though it is not necessary to be completely severed off.

Further, to the shape transferred portion 56 corresponding to the most proximal end portion 11A of the inner layer covering body 51, the reinforcement body 52, and the outer layer covering body 53, the shape of the end surface similar to the shape of the most proximal end portion 11A is transferred by an upper die M3 and a lower die M4 provided with a cavity corresponding to the shape of the end surface of the most proximal end portion 11A. It is preferable that the inner layer covering body 51, the reinforcement body 52, and the outer layer covering body 53 are severed to be completely split in the transverse direction (perpendicular to the central axis of the core rod 40) at the shape transferred portion 56 by the upper die M3 and the lower die M4 reaching the core rod 40, though it is not necessary to be completely severed off. In addition, the most proximal end portion 11A is disposed in the middle portion of the hub 20 in FIG. 1 (there is a space between the end portion of the hub 20 and the outermost base end portion 11A), but is not limited to this configuration. For example, it may be in the same position with the end of the hub 20 and the most proximal portion 11A. Thus, there is an effect guide wire is not caught on the way by the most distal end portion 12A from the end of the hub 20 to form the inner layer seamlessly.

After the shape transferring step, the hydrophilic covering body 54 is formed by coating the outer layer covering body 53 with a hydrophilic polymer material (hydrophilic material) as illustrated in FIG. 4(B) (hydrophilic covering body forming step). The hydrophilic covering body 54 finally constitutes the hydrophilic layer 18 (see FIG. 2) on the outer surface of the catheter tube 10. The hydrophilic layer 18 expresses lubricity when the hydrophilic layer contacts a liquid such as blood or physiological saline, and the friction drag of the catheter tube 10 is reduced, which remarkably improves slidability. As a result, the operability during insertion remarkably improves, and pushability, followability, kink resistance, and safety remarkably improve.

Further, during the insertion of the catheter tube 10 into a blood vessel, it is necessary to hold the proximal end side of the catheter tube 10 by hand to operate. Therefore, the operability is deteriorated when the hand holding the proximal end side of the catheter tube 10 slips, which is not preferable. For such reason, the range, determined by the longitudinal direction of the catheter tube 10, to which the hydrophilic layer 18 is provided, preferably does not include the area extending a distance from the proximal end of the catheter tube 10 toward the distal end, for example a distance of about 150 to 500 mm. Therefore, the hydrophilic covering body 54 coated on the outer circumference surface of the outer layer covering body 53 coats a portion of the outer layer covering body 53 so that the hydrophilic layer 18 is provided in the area mentioned above. Specifically, a plurality of coating ranges B (FIG. 4(B)) corresponding to a portion of the thick portion 41 and the thin portion 42 is provided along the axial direction of the core rod 40 with a given space (i.e., at axially spaced locations), and the hydrophilic covering body 54 is formed on the coating range B.

The hydrophilic polymer material includes natural or synthetic polymer materials as listed below, or derivatives thereof. In particular, cellulose-based polymer materials (e.g., hydroxypropyl cellulose), polyethylene-oxide-based polymer materials (polyethylene glycol), maleic-anhydride-based polymer materials (e.g., maleic anhydride copolymers such as methyl vinyl ether-maleic anhydride copolymer), acrylic-amide-based polymer materials (e.g., polyacrylamide), and water-soluble nylons (e.g., AQ-nylon P-70, produced by Toray Industries, Inc.) are preferable since low friction coefficient can stably be obtained. Among those mentioned above, maleic-anhydride-based polymer materials are far preferably used. Further, a derivative of the polymer material is not limited to a water-soluble material, and not limited if the derivative is constituted based on the polymer material. An insoluble material can be used if the material is hydrous and has a degree of freedom in a molecular chain.

To fix such a hydrophilic polymer material to the outer surface of the catheter tube 10, a covalent bond may preferably be carried out with a reactive functional group which exists or is introduced in the outer layer covering body 53, or on the surface of the outer layer covering body 53. In this manner, a sustainable lubricant surface can be obtained.

The reactive functional group which exists or is introduced in the outer layer covering body 53, or on the surface of the outer layer covering body 53, may be any functional group if the functional group reacts with the hydrophilic polymer material and creates a bond or a cross-link for fixing. For example, such a reactive functional group includes a diazonium group, an azido group, an isocyanate group, an acid chloride group, an acid anhydride group, an imino carbonate ester group, an amino group, a carboxyl group, an epoxy group, a hydroxyl group, and an aldehyde group. Among those mentioned above, an isocyanate group, an amino group, an aldehyde group, and an epoxy group are far preferable as a reactive functional group.

Figure 7:
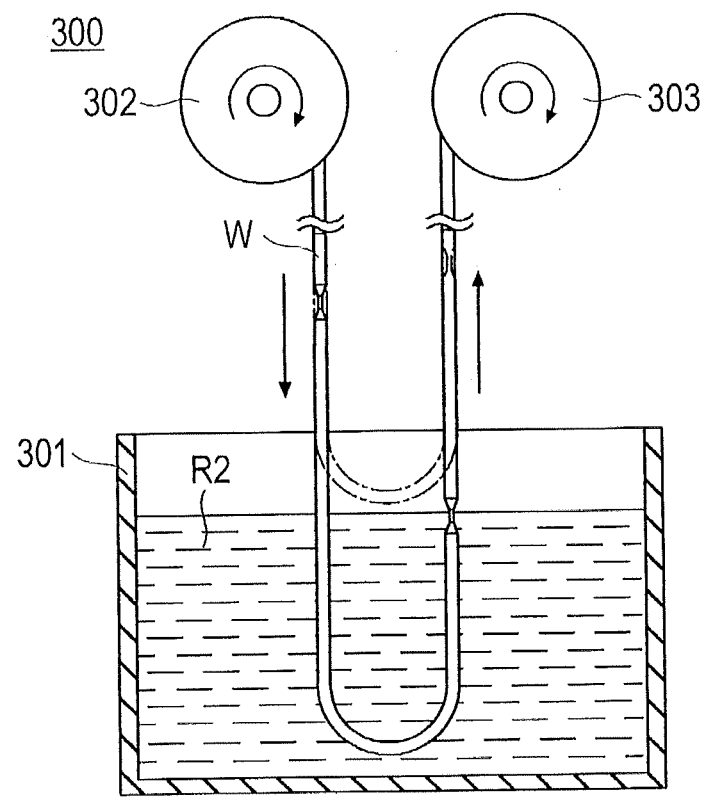
FIG. 7 is a schematic view explaining a method of forming a hydrophilic covering body by dip forming.

In the hydrophilic covering body forming step, the hydrophilic covering body 54 can be formed by dip forming using a structure in which the core rod 40 is coated with the inner layer covering body 51, the reinforcement body 52, and the outer layer covering body 53 as the core material W. An apparatus 300 illustrated in FIG. 7 can be used for dip forming the hydrophilic covering body. The apparatus 300 includes, a container 301 which contains a solution R2 in which a hydrophilic polymer material is dissolved in a solvent, a supply roll 302 which supplies the core material W, and a recovering roll 303 which recovers the core material W coated with the hydrophilic covering body 54. The core material W extends downward from the supply roll 302 and is bent in a U-shape at the bottom end to extend upward so as to reach the recovering roll 303. As a solvent, for example, dimethylformamide, dimethylsulfoxide, tetrahydrofuran, or the like may be applied.

The core material W is coated with the hydrophilic covering body 54 in a manner as follows. The core material W is initially located so that the core material W is spaced from and positioned above the solution R2. Generally speaking, the coating method involves rotating the supply roll 302 while the recovering roll 303 is stopped (i.e., not rotating) so that only the coating range B of the core material W which is to be coated with the hydrophilic covering body 54 is dipped in the solution R2 and coated. With the recovering roller 303 stopped (i.e., not rotating), the supply roller 302 is rotated The core material W is then positioned in the manner shown in FIG. 7, whereupon the supply roll 302 and the recovering roll 303 are stopped (i.e., no longer rotated) material W is fixed by stopping the supply from the supply roll 302 (i.e., stopping rotation of the supply roll 302) and continuing to stop the recovering from the recovering roll 303 (i.e., continuing the stopping of rotation of the supply roll 302). This stopped position in which the rolls 302, 303 do not rotate is illustrated in a dashed line in FIG. 7. Next, the supply roll 302 is rotated to supply the core material W from the supply roll 302 while the recovering roll 303 remains stopped and does not rotate, thus causing the coating range B to be dipped in the solution R2. After a given period of time, the recovering roll 303 is rotated while the supply roll 302 is in a stopped state (i.e., is not rotating) so that the core material W is wound around the recovering roll 303, thereby pulling up the core material W from the solution R2. The coating range B which has just been coated is thus lifted out of the solution R2. The solution R2 adhering to the core material W is air dried or dried by heating with hot air, a heater, or the like so that only the coating range B is coated with the hydrophilic covering body 54. Then, in order to coat the next coating range B, which is spaced from the coating range B previously applied with the hydrophilic covering body 54, the supply roll 302 and the recovering roll 303 are driven or rotated to move the core material W to a position in which only the next coating range B will be dipped in the solution R2. The core material W is then fixed by stopping the supply from the supply roll 302 and stopping the recovering from the recovering roll 303. The above steps are then repeated so that the core material W is coated with successively arranged and axially spaced apart hydrophilic coating bodies 54 with a given space in between successive axially spaced apart coatings. The method of forming the hydrophilic covering body 54 is not limited to the above-described method as the hydrophilic covering body 54 can be formed or applied in other ways. For example, a coating may be formed using a well-known method such as a spray, spraying (spray), application, or printing.

The hydrophilic covering body forming step may be carried out after the proximal end connecting part attaching step, the severing step, the core rod drawing step, or the core rod removing step.

After the hydrophilic covering body forming step, a hub 20 is attached to the portion corresponding to the thick portion 41 of the outer layer covering body 53 as illustrated in FIG. 4(C) (proximal end connecting part attaching step). The hub 20 is arranged on the outer layer covering body 53 by placing hub split portions 20A and 20B, each of which is a circumferentially-split half of the hub 20, to cover the shape transferred portion 56 corresponding to the most proximal end portion 11A of the outer layer covering body 53, and then connecting the hub split portions 20A and 20B together by heat-sealing, an adhesive, or a fastener. In this manner, a tubular continuous body 60 configured with the inner layer covering body 51, the reinforcement body 52, the marker 19, the outer layer covering body 53, the hydrophilic covering body 54, and the hub 20 is formed on the core rod 40. The structure of the tubular continuous body 60 including the core rod 40 is referred to as a continuous body 65 of the catheter tube. The hub may be formed in a shape, for example, with a C cross-section having a slit extending in the axial direction, instead of being provided in a half-split configuration. In the case of the hub having such shape, the hub can be attached to the outer layer covering body 53 via the slit from radially outside of the outer layer covering body 53 to cover the outer layer covering body 53. The slit can be then closed and connected together by heat-sealing, an adhesive, or a fastener. The hub may be formed in a cylindrical shape and be fixed by crimping from outside at a given position after the core rod 40 is inserted in the hub.

Also, the anti-kink protector 30 (proximal end connecting part) may be attached on the outer layer covering body 53 in the proximal end connecting part attaching step using a method similar to that of attaching the hub 20.

After the proximal end connecting part attaching step, the tubular continuous body 60 formed on the core rod 40 is severed together with the core rod 40 at given positions as illustrated in FIG. 4(D) (severing step). The tubular continuous body 60 is severed at a first sever section 63 which is in the vicinity of one of the end portions of the thick portion 41, and at a second sever section 64 on the thin portion 42 in the vicinity of the first sever section 63 in which the thin portion 42 adjoins the transition portion 43 adjoining the first sever section 63 at the opposite side. In this manner, a tubular continuous body 60 is severed to form single tubes or sections 61 each having a long thick portion 41 and a residual tube 62 having a short thick portion 41. The single tubes 61 are an intermediate body which is to become a catheter tube 10, corresponding to one of the catheter tubes 10. The residual tube 62 is removed as an unnecessary portion. As an example of the single tubes or sections 61, the length L1 (FIG. 3(A)) of the portion corresponding to the thick portion 41 of the core rod 40 is 1600 mm and the length L2 (FIG. 3(A)) of the portion corresponding to the thin portion 42 of the core rod 40 is 100 mm.

In the severing step, a cutting blade of, for example, a shearing machine is used for severing. However, any cutting method may be used if the core rod 40 and the tubular continuous body 60 can be severed.

After the severing step, both ends of the single tube 61 severed off in the severing step are fixed to a drawing machine and the whole core rod 40 is drawn (pulled) as illustrated in FIG. 4(E) (core rod drawing step). Then, the core rod 40 is drawn or pulled by the drawing machine until the core rod 40 ruptures at the thin portion 42. The ruptured core rod 40 is pulled out from both sides of the thick portion 41 and the thin portion 42. Since the shape corresponding to each of the most distal end portion 12A and the most proximal end portion 11A is already transferred to each of the shape transferred portions 55 and 56, unnecessary coating bodies 66A and 66B on both sides of the core rod 40 of the single tube 61 can be removed with the core rod 40. In particular, as for the shape transferred portion 56 located inside the hub 20 (see FIG. 4(C)), at least a portion of the inner layer covering body 51, the reinforcement body 52, and the outer layer covering body 53 is already severed at the shape transferred portion 56. Therefore, the unnecessary covering body 66B of which a portion is located inside the hub 20 can also easily be pulled out by simply drawing the core rod 40. By this process, the production of a catheter tube 10 is completed.

The method disclosed here generally involves forming a tubular body (e.g. inner layer 16, reinforcement layer 16 or outer layer 17) on a core rod 40, attaching cylindrically shaped proximal end connecting parts to the radially outer side of the tubular body so that the cylindrically shaped proximal end connecting parts are axially spaced apart from one another along the axial extent of the tubular body, and then severing the core rod and the tubular body at a plurality of axially spaced apart locations to sever the core rod with the tubular body into a plurality of separated sections which each include a portion of the core rod covered by a portion of the tubular body and one of the proximal end connecting parts attached to the radially outer side of the portion of the tubular body. The core rod is then removed from each of the sections to result in the catheter tubes in which the proximal end connecting part is the hub which is fixed to the proximal end portion of the catheter tube. More specifically, as described above, the method of producing the catheter tube 10 according to an embodiment disclosed here by way of example includes the covering body forming step (inner layer covering body forming step and outer layer covering body forming step) in which the covering body (inner layer covering body 51 and outer layer covering body 53) is formed by coating the core rod 40 with resin, the proximal end connecting part attaching step in which the cylindrically shaped hub 20 connected to the proximal end of the catheter tube 10 is attached to the radially outer side of the inner layer covering body 51 and the outer layer covering body 53 with a given space, the severing step in which the tubular continuous body 60 obtained on the core rod 40 is severed at a given position after the proximal end connecting part attaching step into the plurality of single tubes 61 each provided with the hub 20, and the core rod removing step in which the core rod 40 is removed from the single tube 61. As described above, in the method of production, the inner layer covering body 51 and the outer layer covering body 53 are coated on the core rod 40 and then the hubs 20 are attached at predetermined intervals. The tubular continuous body 60 obtained on the core rod 40 is then severed at a given position into the plurality of single tubes 61 each provided with the hub 20. Therefore, it is not necessary to reposition the already severed off single tube 61 to attach the hub 20 on the single tube. Thereby, the number of repetitions of positioning for the operation can be reduced. Consequently, a plurality of catheter tubes 10 can continuously be produced using the same core rod 40, thereby enabling efficient production of the catheter tube 10.

As for a method of producing a catheter tube, a heat drawing process is conventionally used, in which the heat drawing process is applied to a tubular body to reduce the inner and the outer diameter through the proximal end side to the distal end side. However, when a heat drawing process is applied, during a heat-melt process for attaching a soft tip or an imaging marker, or the like, a residual strain produced by the heat drawing process causes the inner and the outer diameter in the vicinity of the melt zone to increase and deteriorates the dimensional accuracy. As a result, there arises a problem such as yield deterioration. On the contrary, in the method of production according to the embodiment, a heat drawing process is not applied so that the method of production is free of strain produced by drawing, thereby improving processability and, as a result, reducing cost. Further, since there is no increase in the winding pitch (grid interval of braiding) of the reinforcement body 52 caused by drawing, excellent flexibility and kink resistance of the distal end side are provided.

Further, before the proximal end connecting part attaching step, the shape transferring step, in which the shapes corresponding to the shape of the most distal end portion 12A and the most proximal end portion 11A of the catheter tube 10 are transferred to the inner layer covering body 51 and the outer layer covering body 53 with a given space, is included. Therefore, the shape of the portion, in which the hub 20 is to be attached, is transferred before the hub 20 is attached, thereby enabling further efficient production of the catheter tube 10.

Further, since the thick portion 41 and the thin portion 42, each having an outer diameter different from each other, are continuously formed in advance with a given space between the two on the core rod 40, a catheter tube 10 having a different diameter at the distal end portion and the proximal end portion can efficiently be produced using the continuously lined tubular continuous body 60. By using the tube proximal end portion 11, having a large diameter, as a proximal end side, and using the tube distal end portion 12, having a small diameter, as a distal end side, the distal end is provided with flexibility without deteriorating pushability and fluid-transferability of the proximal end side, thereby providing excellent guide wire followability and kink resistance to the produced catheter tube 10.

Further, since the covering body forming step includes the inner layer covering body forming step in which the inner layer covering body 51 is formed by coating a resin on the core rod 40 so as to be in contact therewith, and the outer layer covering body forming step in which the outer layer covering body 53 is formed by coating a resin on the radially outer side of the inner layer covering body 51, the hub 20 can efficiently be attached to the catheter tube 10 having a multilayer structure.

Further, since the reinforcement body forming step, in which a reinforcement body 52 configured with a wire is formed so as to be in contact with the inner layer covering body 51 and the outer layer covering body 53, is further included before the proximal end connecting part attaching step, the catheter tube 10 to be produced can be locally reinforced as desired, thereby improving pushability and kink resistance.

Further, the continuous body of a catheter tube 65 includes the core rod 40, the covering body (inner layer covering body 51 and outer layer covering body 53) which is formed on the core rod 40 by coating a resin on the core rod, and a cylindrically shaped hub 20 (proximal end connecting part) attached to the radially outer side of the inner layer covering body 51 and the outer layer covering body 53 with a given space along the axial direction of the core rod 40. The continuous body 65 already has the hub 20 attached to the continuous body 65 with a given space before being severed. Therefore, it is not necessary to reposition the single tube 61 to attach the hub 20 to the already severed off single tube 61, thereby reducing the number of repetition of positioning for operation and thus enabling more efficient production of the catheter tube 10.

The present invention is not limited to the embodiment described above, and various modifications can be made by those skilled in the art within a scope of the technical idea of the present invention. For example, in the embodiment, the shapes are transferred to both the inner layer covering body 51 and the outer layer covering body 53 in the shape transferring step, though the shapes may be transferred to only either of them.

Figure 8:
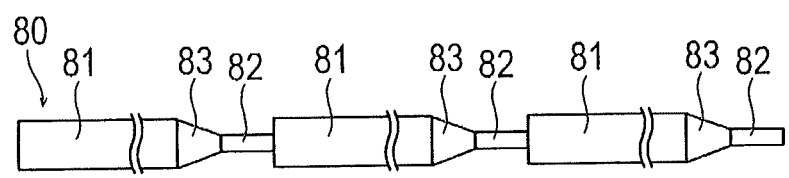
FIG. 8 is a plan view illustrating a modification of a core rod.

Further, the transition portion 83 between the thick portion 81 and the thin portion 82 may be provided only in one end side of the thick portion 81, like a core rod 80 illustrated in FIG. 8 as an example of a modification. In this case, the length of the residual tube (see the residual tube 62 in FIG. 4(D)) which is to be removed after being severed off is short, which may contribute to cost reduction and saving of production space.

Figure 9:
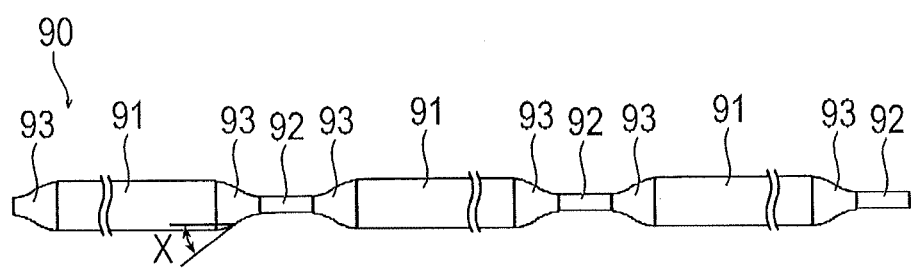
FIG. 9 is a plan view illustrating another modification of a core rod.

Further, at least a portion of the outer circumference surface of the transition portion 93 may be formed of a curved line, when seen from the longitudinal cross-section along the axis of the core rod 90, like a core rod 90 illustrated in FIG. 9 as an example of another modification. In this manner, the stiffness of the catheter tube to be produced changes relatively smoothly and slopingly along the axis, which restrains a local bent, thereby enabling the production of the catheter tube having excellent pushability and kink resistance. In FIG. 9, the slope angle X of the outer circumference surface of the transition portion 93 which is defined in the longitudinal cross section along the axis of the core rod 90 gradually increases along the axial direction starting from the thin portion 92 toward the thick portion 91. The slope angle X is at maximum at the almost center portion of the transition portion 93, and gradually decreases along the axial direction further approaching the thick portion 91. By virtue of being formed in this shape, the stiffness of the portion between the thick portion 91 and the thin portion 92 can be changed further smoothly and slopingly along the axial direction, thereby enabling the production of the catheter tube having further excellent pushability and kink resistance.

Further, a radiopacity marker may be arranged between the inner layer covering body 51 and the reinforcement body 52, between the outer layer covering body 53 and the reinforcement body 52, or on the outer layer covering body 53. Further, each of the reinforcement body 52, the outer layer covering body 53, the hydrophilic covering body 54, the marker 19, and the hub 20 need not necessarily be provided.

Further, a hardening treatment may be provided to at least one of the inner layer covering body 51 and the outer layer covering body 53 by irradiating an electron ray or a gamma ray to bridge the material to increase hardness. Further, a softening treatment may be provided to at least one of the inner layer covering body 51 and the outer layer covering body 53 to reduce hardness by using an acid or an alkali.

The cross-sectional shape of the catheter tube 10 in the section perpendicular to the axis may be, for example, an oval or the like, instead of a circle. Further, the cross-sectional shape of the lumen 14 of the catheter tube 10 in the section perpendicular to the axis may be, for example, an oval, a half circle, or the like, instead of a circle. Further, a plurality of lumen may be provided to the catheter tube 10.

The detailed description above describes a method of producing a catheter tube and a continuous body of a catheter tube which is used for a catheter. The method and the continuous body are disclosed by way of example. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of producing catheter tubes each possessing a distal end portion and a proximal end portion at which is fixed a hub, the method comprising:
    forming a tubular body on a core rod, the tubular body possessing an axial extent;
    attaching a plurality of cylindrically shaped proximal end connecting parts to a radially outer side of the tubular body;
    so that the cylindrically shaped proximal end connecting parts are axially spaced apart from one another along the axial extent of the tubular body;
    severing the core rod and the tubular body at a plurality of axially spaced apart locations after attaching the cylindrically shaped proximal end connecting part to the radially outer side of the tubular body to sever the core rod with the tubular body into a plurality of separated sections which each include a portion of the core rod covered by a portion of the tubular body and one of the proximal end connecting parts attached to the radially outer side of the portion of the tubular body; and
    removing the core rod from each of the sections to result in the catheter tubes in which the proximal end connecting part is the hub which is fixed to the proximal end portion of the catheter tube.

2. The method of producing catheter tubes according to claim 1, further comprising transferring a shape corresponding to a shape of the distal end portion of the catheter tube is transferred to the tubular body, before attaching the proximal end connecting parts to the radially outer side of the tubular body.

3. The method of producing catheter tubes according to claim 1, wherein the core rod, before forming the tubular body on the core rod, possesses a relatively thicker portion and a relatively thinner portion, each having a different outer diameter, the relatively thicker portion and the relatively thinner portion being spaced apart from one another along the axial extent of the core rod.

4. The method of producing catheter tubes according to claim 1, wherein the tubular body possesses an inner layer that contacts an outer surface of the core rod and an outer layer onto a radially outer side of the inner layer.

5. The method of producing catheter tubes according to claim 4, the forming of the tubular body further comprising applying a reinforcement wire before attaching the plurality of cylindrically shaped proximal end connecting parts so that the reinforcement wire is embedded between the inner layer and the outer layer in the tubular body.

6. The method of producing catheter tubes according to claim 5, further comprising removing a portion of the reinforcement wire after the reinforcement wire is applied on the outer side of the inner layer.

7. The method of producing catheter tubes according to claim 1, wherein the removing of the core rod from each of the sections comprises applying a pulling force to opposite ends of the core wire to rupture the core rod.

* * * * *